(12) United States Patent
Griswold et al.

(10) Patent No.: US 9,274,187 B2
(45) Date of Patent: Mar. 1, 2016

(54) MAGNETIC RESONANCE IMAGING (MRI) SCAN PLANE CONTROL DEVICE

(71) Applicant: Case Western Reserve University, Cleveland, OH (US)

(72) Inventors: Mark Griswold, Shaker Heights, OH (US); Matthew Riffe, Cleveland Heights, OH (US); Michael D. Twieg, Cleveland, OH (US)

( * ) Notice: Subject to any disclaimer, the term of this patent is extended or adjusted under 35 U.S.C. 154(b) by 89 days.

(21) Appl. No.: 14/329,973

(22) Filed: Jul. 13, 2014

(65) Prior Publication Data

US 2016/0011285 A1   Jan. 14, 2016

(51) Int. Cl.
*A61B 5/055*   (2006.01)
*G01R 33/28*   (2006.01)
*G01R 33/54*   (2006.01)

(52) U.S. Cl.
CPC ............ *G01R 33/286* (2013.01); *A61B 5/0555* (2013.01); *G01R 33/543* (2013.01)

(58) Field of Classification Search
CPC ............... A61B 2019/2292; A61B 2019/5236; A61B 2019/5251; A61B 2019/5289; A61B 5/055; A61B 5/062; A61B 5/721
See application file for complete search history.

(56) References Cited

U.S. PATENT DOCUMENTS

| | | | | |
|---|---|---|---|---|
| 2003/0192557 A1* | 10/2003 | Krag | ...................... | A61B 19/52 128/898 |
| 2008/0039717 A1* | 2/2008 | Frigg | ...................... | A61B 19/54 600/424 |

* cited by examiner

*Primary Examiner* — Mark Remaly

(57) ABSTRACT

Example devices, apparatus, and methods concern intervention-independent imaging control for an MRI system. A hand wearable device (e.g., glove) that can be manipulated independently of an interventional device (e.g., catheter) in use to treat a patient transmits position signals describing an orientation of the device to an MRI system. The device may have fiducial markers mounted on an operator's fingers. The MRI system determines a desired scan plane that will correspond to the orientation of the intervention-independent device and performs a diagnostic scan on the desired scan plane. The spatial proximities of the markers may control a switch based control that controls image acquisition parameters including field of view.

22 Claims, 9 Drawing Sheets

MAGNETIC RESONANCE IMAGING (MRI) SCAN PLANE CONTROL DEVICE

BACKGROUND

Magnetic resonance imaging (MRI) systems are frequently employed to provide guidance to interventionalists who are performing interventional procedures to diagnose or treat tissue in a patient. During interventional procedures, an interventional device (e.g., catheter) may be guided by an interventionalist (e.g., surgeon, radiologist) to a target tissue (e.g., tumor) or target area (e.g., heart) in a patient. Interventional devices may include, for example, needles, catheters, ablation devices, imaging devices, therapeutic devices, diagnostic devices, or other devices. These interventional devices are intracorporeal devices that may be maneuvered inside a patient's body. In an image guided interventional device insertion, the location of the device relative to the surrounding anatomy and target area are determined using the MRI system.

To assist in MRI image guided interventional procedures, techniques have been developed that track the location of an interventional device during the procedure. These techniques may update scan planes used by the MRI system so that the scan planes automatically track the device. Conventional methods and apparatus localize multiple markers with fixed positions on the apparatus. For example, optical tracking employs multiple cameras with different positions and orientations to measure the locations of optical markers. The optical markers may be reflective and the optical tracking apparatus may be self-contained and wireless. However, optical tracking is less than optimal for at least the reason that the optical markers must remain visible to the cameras throughout the entire procedure. By being forced to remain visible to the cameras, optical tracking limits the freedom of the interventionalist to freely wield the interventional device inside the magnet bore.

Other conventional techniques employ tuned coils containing fiducial markers. For example, passive fiducial marker tracking uses the signal enhancement produced by individual tuned coils that couple directly to a local fiducial marker. The fiducial markers are localized using specific sequence parameters to enhance the signal of the passive fiducial marker, while only slightly perturbing surrounding signal sources. While passive fiducial marker tracking allows an apparatus to be wielded more freely in the bore of the magnet of an MRI system without regard to camera visibility, the enhanced marker visibility and localization is highly dependent on a number of parameters. These parameters, which include the marker position and orientation, limit the ability of the interventionalist to freely wield the interventional device in the bore. In contrast, active fiducial marker tracking directly connects tuned coils containing fiducial markers to the magnetic resonance (MR) scanner. Active fiducial marker tracking treats the tuned coils as standard coils, which allows for easy integration with the MR system. Additionally, the apparatus can be localized regardless of marker orientation and position as long as the marker remains within the bore's imaging region. However, the markers must be connected to the MR system, which in conventional systems is achieved by coaxial cables. Unfortunately, the coaxial cables may hinder the interventionalist's ability to freely wield the device. Furthermore, coaxial cables snaking about the core may present safety issues for the patient.

While passive fiducial marker tracking and active fiducial marker tracking offer some improvements over optical tracking, both active and passive fiducial marker tracking have their own limitations. In some circumstances these techniques, which fix the scan plane relative to the interventional device, produce unsatisfactory results. For example, flexing of a catheter or needle on an interventional device may cause misregistration of the scan plane to the tissue in treatment. In other instances, the interventionalist performing the procedure may wish to view an image that does not correspond to a scan plane in the fixed relationship to the interventional device. When a different scan plan is desired, a time consuming manual adjustment of the scan plane is performed. In some clinical situations, when a patient is confined in an MRI apparatus during a procedure (e.g., heart ablation), it may be desirable to reduce time spent making adjustments.

BRIEF DESCRIPTION OF THE DRAWINGS

The accompanying drawings, which are incorporated in and constitute a part of the specification, illustrate various example devices, methods, apparatus and other embodiments of various aspects of the invention. It will be appreciated that the illustrated element boundaries (e.g., boxes, groups of boxes, or other shapes) in the figures represent one example of the boundaries. In some embodiments one element may be designed as multiple elements, multiple elements may be designed as one element, an element shown as an internal component of another element may be implemented as an external component and vice versa, and so on. Furthermore, elements may not be drawn to scale.

DETAILED DESCRIPTION

Example devices, methods, and apparatus facilitate an interventionalist (e.g., surgeon) controlling a magnetic resonance imaging (MRI) system in a manner that is intervention-independent. While an interventionalist may be a surgeon, doctor, nurse, radiologist or other medical personnel, the more specific term "surgeon" will be used interchangeably with the more general term "interventionalist". Example devices, methods, and apparatus facilitate specifying a desired scan plane in a manner that is intervention-independent. In this context, intervention-independent scan plane control means that the scan plane is not automatically determined in relation to any interventional device, but rather is specified by the surgeon substantially in real-time using a wearable device. The surgeon may decide on a scan plane based, for example, on tactile feedback received from a needle or catheter that the surgeon or other team member is manipulating in the patient (e.g., human, horse, cat, dog). Example devices, methods, and apparatus also facilitate a surgeon controlling image acquisition parameters in a manner that is intervention-independent.

Intervention-independent scan control can be performed regardless of whether an interventional device is in use on the patient because the scan plane is not determined relative to an interventional device. To realize intervention-independent scan plane control, a wireless hand-wearable intervention-independent device for specifying a scan plane is provided. A method of controlling an MRI system to acquire an image according to an intervention-independent scan plane and an MRI system for performing imaging based on an intervention-independent scan plane are also provided. A method of controlling an MRI system to acquire an image according to image acquisition parameters defined in a manner that is intervention-independent is also provided.

Figure 1:
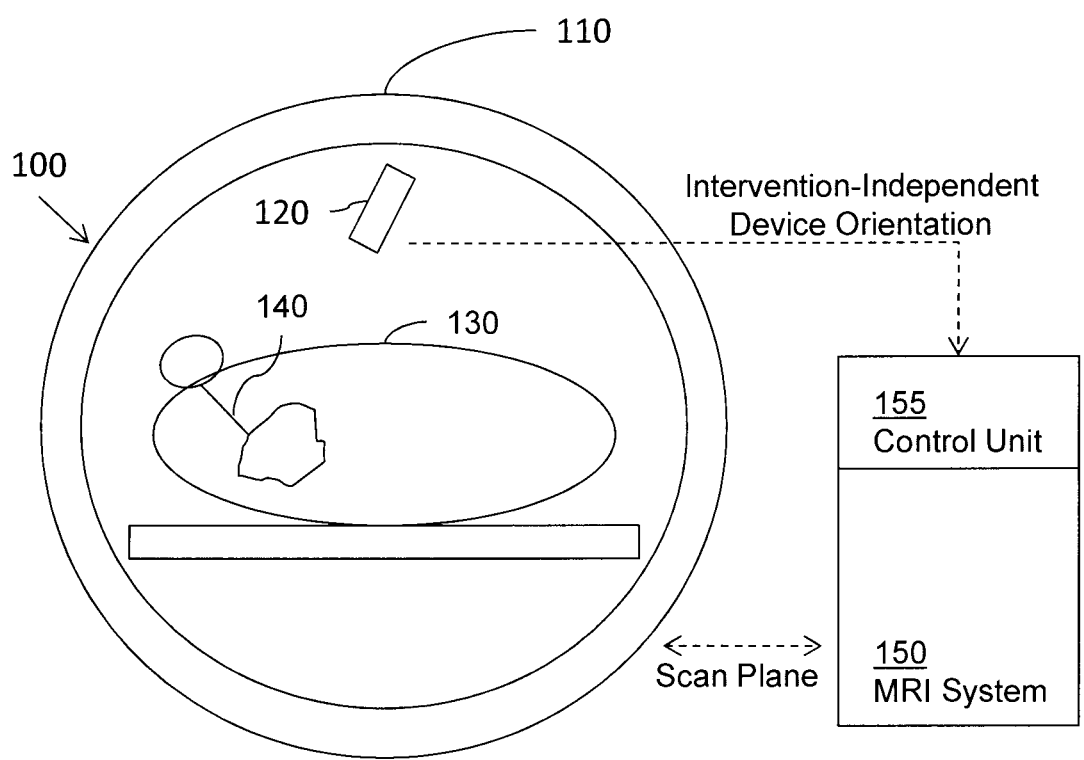
FIG. 1 schematically illustrates an embodiment of an MRI apparatus that includes a device for magnetic resonance imaging (MRI) control.

FIG. 1 is a schematic illustration of an embodiment of a system 100 that employs intervention-independent MRI control. System 100 employs intervention-independent scan plane control and intervention-independent image acquisition parameter control. A patient 130 and an interventional device 140 being used to access tissue in the patient 130 are shown located in a bore of an MRI magnet 110. A hand-wearable intervention-independent device 120 is being manipulated by a surgeon to specify a desired scan plane in which an MRI system 150 should image. Signals corresponding to an orientation of the hand-wearable intervention-independent device 120 are transmitted wirelessly from the hand-wearable device 120 to an MRI control unit 155 that is part of the MRI system 150. The control unit 155 converts the information about the orientation of the hand-wearable device 120 into a desired scan plane. The MRI system 150 is controlled to produce an image of the patient 130 along the desired scan plan.

Hand-wearable intervention-independent device 120 may be manipulated by the surgeon during imaging to specify image acquisition parameters. Signals corresponding to an orientation of the hand-wearable intervention-independent device 120 are transmitted wirelessly from the hand-wearable device 120 to MRI control unit 155. Control unit 155 employs information about the orientation of the hand-wearable device to control image acquisition parameters. For example, as a surgeon rotates her hand, markers on a glove worn by the surgeon may also rotate. The position of the markers may be used to control MRI parameters including the scan plane.

The images produced by the MRI system 150 may be used by the surgeon to guide the interventional device 140 in the patient 130. For example, the surgeon may be performing an MRI guided biopsy. As the surgeon advances the needle towards a target region (e.g., lesion, tumor, mass, volume) with one hand, the surgeon may control the MR scan plane by manipulating the hand-wearable intervention-independent device 120 with the other hand. To assist in navigating the needle, the surgeon may manipulate the device 120 to control desired image acquisition parameters. For example, while navigating the needle, the surgeon may manipulate the device 120 to control the MRI system 150 to provide a wide field of view (FOV). When the needle approaches the target region, the surgeon may manipulate the device 120 to control the MRI system 150 to provide a more narrow FOV. By way of illustration, as the surgeon approaches critical locations in the vasculature (e.g., branch points), the surgeon may want a higher resolution image with a smaller FOV to facilitate guiding the catheter to a desired location. But when the surgeon is advancing the catheter through a portion of the vasculature that does not have any branch points, the surgeon may want a lower resolution image with a larger FOV to facilitate keeping a mental image of the overall location of the catheter.

Figure 2:
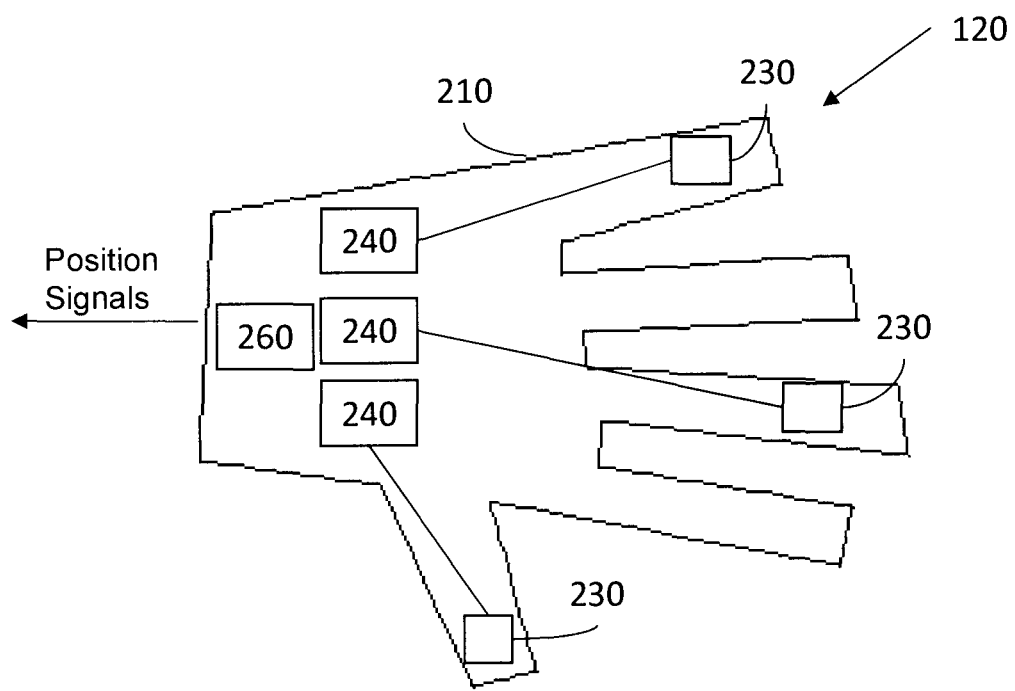
FIG. 2 schematically illustrates an embodiment of a hand-wearable device for MRI control.

FIG. 2 illustrates an embodiment of the hand-wearable intervention-independent device 120. Device 120 includes a plurality of markers 230 that produce position signals corresponding to positions of the markers 230. The position signals produced by markers 230 describe an orientation of device 120. The position signals are magnetic resonance (MR) signals from which the spatial coordinates of a member of markers 230 can be determined. The orientation of the device 120 can also be determined from the position signals. Markers 230 may be active markers that are responsive to excitation from an MRI magnetic field to produce the position signals. In one embodiment, hand-wearable intervention-independent device 120 includes three markers 230 that produce position signals corresponding to positions of the markers 230. The position signals produced by the markers 230 are sufficient to describe a desired scan plane for an MRI imaging system. The markers 230 are connected to wireless transmitters 240. The position signals may be typical MR image signals that are used by the MRI system to determine spatial coordinates of the markers. While three markers 230 are shown in FIG. 2, other numbers of markers that can sufficiently describe a desired scan plane may be used. In one embodiment, the markers 230 are mounted distally to the proximal interphalangeal joints of the fingers of the surgeon. For example, the markers 230 may be mounted to the dorsal side of the surgeon's fingers within a threshold distance of the surgeon's fingertips and thumb tip. Thus, the markers 230 may be positioned with non-uniform uniform spacing between them. This non-uniform spacing facilitates distinguishing individual markers 230 based on their relative positions.

Hand-wearable intervention independent device 120 may also include an onboard asynchronous reference source 260. Device 120 generates its own onboard asynchronous reference signal using onboard asynchronous reference source 260. In one example, the asynchronous reference signal is asynchronous to a synchronization signal provided by an MR scanner with which device 120 is interacting. In one example, the onboard asynchronous reference source 260 may be a ceramic oscillator. Device 120 may be employed in an MRI bore and thus be subjected to intense magnetic fields (e.g., 1.5 T, 3 T, 7 T). In one example, the ceramic oscillator may be a 5 MHz ceramic oscillator. In another, the ceramic oscillator may be a 10 MHz ceramic oscillator. Other frequencies (e.g., 20 MHz) may be employed in other embodiments. In one example, the ceramic oscillator will produce a signal whose frequency shift error is less than 20 ppm. Signals with other qualities (e.g., frequency shift error up to 100 ppm) may be generated. In one embodiment, the onboard asynchronous reference source 260 produces a carrier frequency to facilitate transmitting the position signals to the MR scanner with which device 120 is interacting.

In one embodiment, hand-wearable intervention-independent device 120 includes a housing 210. Housing 210 houses the markers 230, the transmitters 240, and the onboard asynchronous reference source 260. Housing 210 is wearable on a hand or a wrist of a surgeon performing an MRI-aided intervention on a patient. Housing 210 mounts a marker 230 distally to a proximal interphalangeal joint of a surgeon's finger. Housing 210 also mounts a marker 230 distally to a proximal interphalangeal joint of the surgeon's thumb. Housing 210 mounts transmitters 240 within a threshold distance of the surgeon's wrist.

In one embodiment, housing 210 is a glove that may be worn on a surgeon's hand. Markers 230 mounted on housing 210 are able to move within a threshold of the degree of freedom of movement of the surgeon's hand. For example, housing 210 may be flexible enough to allow the surgeon to move the markers 230 throughout the entire range of motion of the surgeon's fingers. When moved in correspondence to the movements of the surgeon's fingertips, the markers 230 may produce different position signals that are sufficient to describe a different desired scan plane for an MRI system. For example, the surgeon may hold her or his (her) fingers steady relative to each other, but may rotate her hand about an axis approximately parallel to her forearm, thus moving the markers 230 and describing a different desired scan plane. In another example, the surgeon may hold her hand steady in a position relative to the patient but may manipulate her fingers, thereby altering the positions of the markers 230 relative to each other, and thus describing another different desired scan plan. The motions of the markers 230 are limited only by the available space in the magnet bore and by the physical range-of-motion limitations of the surgeon's hand and fingers within the bore.

Figure 9:
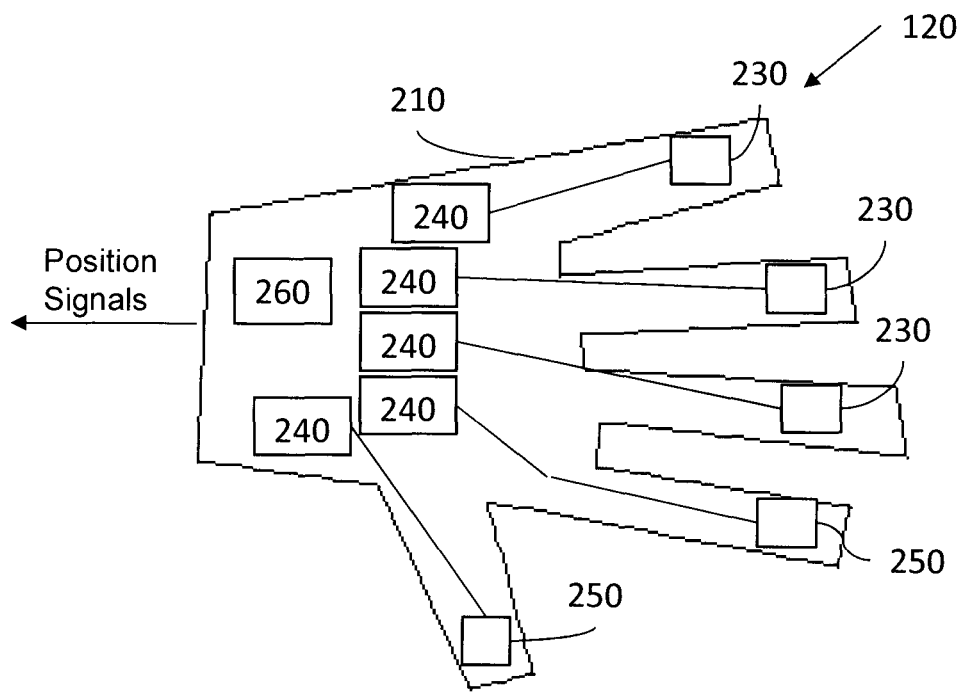
FIG. 9 schematically illustrates an embodiment of a hand-wearable device for intervention-independent MRI control.

FIG. 9 illustrates another embodiment of the hand-wearable intervention-independent device 120. While device 120 is described as being hand-wearable, in different embodiments the device may be mountable on a surgeon's hand or arm, may be affixed to a surgeon's hand or arm, or may be associated with the surgeon in other ways. This embodiment of device 120 includes a switch-based control. In FIG. 9, note that markers 230 are now mounted on the little finger, ring finger, and middle finger of the housing 210. Markers 250 are mounted on the index finger and thumb of the housing 210. Spatial proximities of markers 250 are derived from the position signals of markers 250. In one example, the switch based control is controlled by the spatial proximities associated with markers 250. In this example, markers 230 define the desired scan plan, while the surgeon's index finger and thumb mount markers 250. Since markers 250 are mounted on different fingers than markers 230, the fingers of the surgeon mounting markers 250 are free to control the switch-based control independently of the positions of markers 230.

The switch-based control may control image acquisition parameters. The switch-based control may control, for example, the field of view (FOV) of the MRI device 150 (FIG. 1). In other examples, other image acquisition parameters may be controlled by the switch-based control. In this example, when the markers 250 mounted on the index finger and thumb of the surgeon are spatially positioned more than a threshold distance apart, the switch based control may detect the position signals associated with the markers 250 and control the MRI device 150 to display a wide FOV. When the markers 250 are brought to within a threshold distance of each other, the switch based control may control the MRI device 150 to display a narrow FOV. In one embodiment, gestures made with the fingers (e.g., pinch, spread) may control the FOV. In another example, bringing two of the markers 250 to within a threshold distance of each other may cause the switch-based control to control the MRI device 150 (FIG. 1) to change a different image acquisition parameter. The image acquisition parameter may concern, for example, phase encoding, frequency encoding, pulse sequence, repetition time, echo time, number of signal averages, or other parameters. Other spatial position relationships between markers 250 may be employed to control the switch-based control. For example, rapidly moving markers 250 to within a threshold distance of each other two times in a row within a threshold period of time may cause the switch-based control to cycle through different image acquisition parameters. In this example, rapidly bringing the index finger and the thumb together two times in a row within a threshold period of time may act like double-clicking a computer mouse, double clicking a laptop computer control pad, or double tapping a tablet computer display. Other arrangements of markers 230 and markers 250 may be employed depending on the surgeon's preferences. Thus, the surgeon can manipulate the interventional device with one hand while simultaneously controlling both the scan plane and image acquisition parameters with her other hand.

Figure 3:
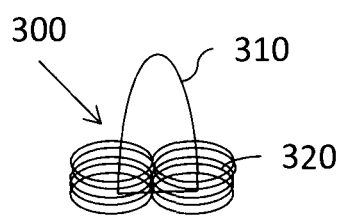
FIG. 3 schematically illustrates an embodiment of an active tracking marker that can be used in a device for MRI control.

FIG. 3 is a schematic illustration of an active marker 300. The markers 230 (FIG. 2) may be active markers like active marker 300. Active marker 300 responds to excitation from the MRI magnetic field with which it interacts to produce the position signals. The active marker 300 includes a fiducial marker 310 coupled to a microcoil 320. The fiducial marker 310 may be a vitamin E capsule or other fluid filled vessel that will properly respond to the magnetic field of an MRI apparatus with which marker 300 interacts. The microcoil 320 may be, for example, a multi-turn butterfly coil, gradiometer, or other configuration that provides a signal in all positions relative to the magnetic field. Traditional coils will not produce a signal when aligned perfectly with the magnetic field. When employed with device 120 (FIG. 2) or other wearable devices, microcoil 320 improves on conventional systems by not restricting the orientations in which the surgeon may place the device 120 while defining a desired scan plane. In one embodiment, microcoil 320 includes a plurality of orthogonal solenoid coils connected in series. In this embodiment, the plurality of orthogonal solenoid coils are wrapped around the fiducial marker 310.

Referring back to FIG. 2, the intervention-independent device 120 also includes three transmitters 240 that transmit the position signals produced by the markers 300 to an MRI system. While one transmitter per marker is shown in FIG. 2, different numbers of transmitters could be used. For example, in FIG. 9, five transmitters 240 are shown. Three of the five transmitters 240 may be connected to and associated with markers 230 while two other of the transmitters 240 may be associated with markers 250. The intervention-independent device 120 may also include additional electronic and mechanical components including signal conditioning components (e.g., on-board amplifiers) and a power source. In one embodiment, the power source is a lithium-ion battery. In one embodiment, the intervention-independent device 120 is wireless.

In one example, wireless device 120 and the transmitters 240 wirelessly transmit the position signals to an MRI imaging system using amplitude modulation (AM). In another example, the transmitters 240 wirelessly transmit the position signals to the MRI imaging system using frequency modulation (FM). In another example, the transmitters 240 wirelessly transmit the position signals to the MRI system using a spread spectrum approach. In another example, transmitters 240 that transmit using AM, FM and/or spread spectrum may be employed and the surgeon may choose which type of modulation to employ. One example MRI system that has been developed to wirelessly receive image signals from multiple channels simultaneously using amplitude modulation encoding is described in "Using On-board Microprocessors to Control a Wireless MR Receiver Array." Matthew J. Riffe, Jeremiah A. Heilman, Natalia Gudino, Mark A. Griswold, Using On-Board Microprocessors to Control a Wireless MR Receiver Array, Proceedings 17th Scientific Meeting, International Society for Magnetic Resonance in Medicine 2009: 2936. By wirelessly transmitting and receiving signals, device 120 improves on conventional systems by removing the need for coaxial or other types of cables that foul the interior of the MR bore. Removing unnecessary cables from the bore prevents artifacts from being produced by the cables on the MR images, reduces patient discomfort, and allows the surgeon more freedom to move her hands in the bore.

Unlike conventional devices, the intervention-independent device 120 transmits position signals that describe a desired scan plane without signal or mechanical interaction with an interventional device that may be in use to treat a patient. For example, the surgeon can use her hand to control the scan plane regardless of what is happening with the catheter. For example, the surgeon may have been moving a catheter through an artery during a planned heart ablation procedure but may have noticed an aneurism along the way. Thus, the surgeon may stop advancing the catheter to prevent rupturing the aneurism. The surgeon may decide to do pre-surgical planning to treat the aneurism. The pre-surgical planning may include acquiring multiple MR images at different scan planes and with different parameters. Controlling the pre-surgical planning by manipulating the glove is independent of the catheter. In this example, being "independent of the catheter" means that signals from the catheter are not used to determine or control the scan plan. Instead, signals from the device 120 are used to determine or control the scan plan. The desired scan plane described by the position signals is used by the MRI system 150 (FIG. 1) to perform a subsequent scan of the patient independent of a position of the interventional device. To facilitate ease of manipulation, the markers 230, markers 250, or transmitters 240 may be located in a housing 210 that is worn on the hand or wrist. In one embodiment, the markers 230 and 250 are located on the dorsal fingertips of a glove. In other embodiments, the markers 230 and 250 may be located in other positions relative to the surgeon's hand. While no direct interaction between the interventional device (e.g., catheter) and the intervention-independent device 120 (e.g., glove with markers and transmitters) exists, an indirect interaction may be mediated by the surgeon. The interventional device may be, for example, a catheter, a needle, an ablation device, an imaging device, a therapeutic device, a diagnostic device, or other apparatus.

Figure 4:
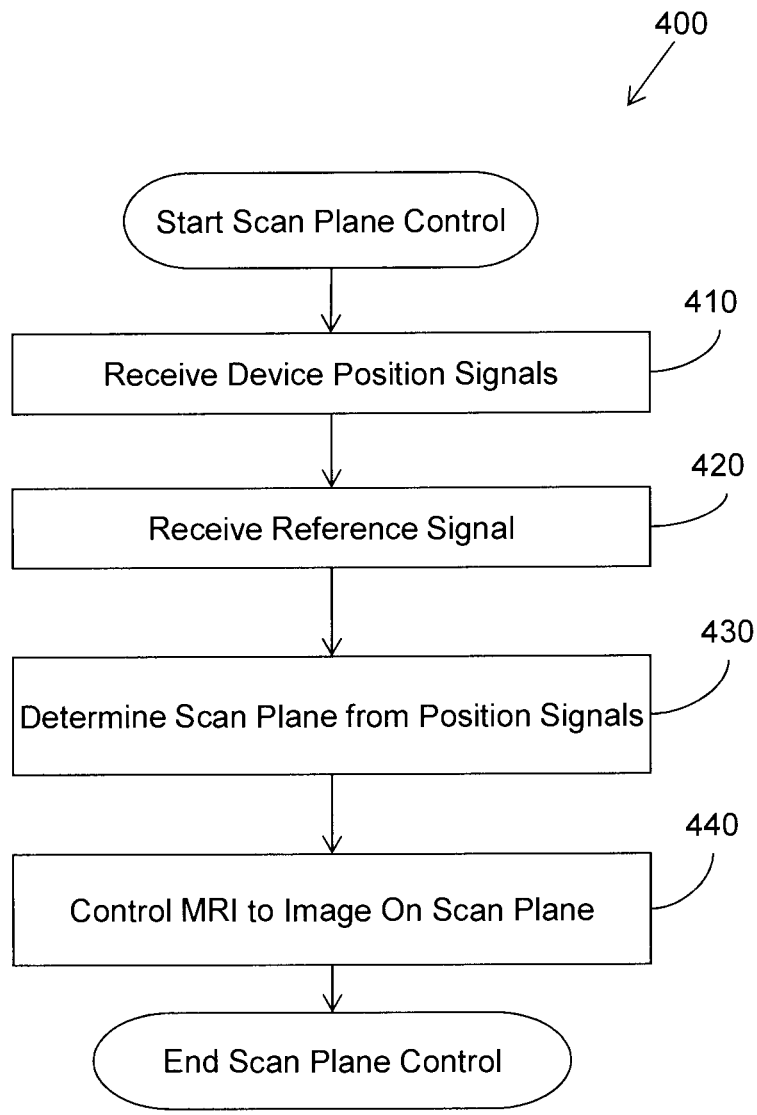
FIG. 4 is a flow diagram that illustrates an example method for performing MRI control.

FIG. 4 illustrates an example method 400 for performing intervention-independent scan plane control using signals generated by a wearable device. The method 400 may be performed by an MRI control unit 155 (FIG. 1). Method 400 may also be performed by a computer. Method 400 includes, at 410, receiving device position signals. The position signals may be received from a hand-wearable intervention-independent device. The device position signals may be received while the device is being manipulated independently of an interventional device being used to treat a patient. The device position signals describe an orientation of the intervention independent device and may also describe how markers on the device are being moved. For example, a surgeon may be guiding a catheter with her right hand while wearing an example glove on her left hand. As the surgeon guides the catheter she may want to change the FOV for an MR image that is being acquired during the procedure. The surgeon may move the fingers on her left hand to control the MRI apparatus that is acquiring the MR image.

The position signals may be AM signals that are wirelessly received. The AM signals may describe an orientation of the intervention-independent device. The position signals may also be FM signals that are wirelessly received. The FM signals may describe an orientation of the intervention-independent device. Recall that the hand-wearable intervention-independent device (e.g. glove, mitten, gauntlet) includes a plurality of markers. The plurality of markers may include a first set of three or more markers that are mounted distally from the proximal interphalangeal joints of the surgeon. The position signals may provide information about the locations of the markers.

At 420, method 400 includes wirelessly receiving a reference signal from the hand-wearable intervention-independent device. The device (e.g., glove) may be manipulated independently of an interventional device (e.g., catheter) that is being used in a patient. The reference signal may be used to synchronize the position signals received from the device with the MRI system with which the device is interacting. Receiving a reference signal may include receiving a mixed signal that includes high frequency upper and lower side band frequencies for a low frequency reference signal. Receiving a reference signal may also include reconstructing the low frequency reference signal by mixing the upper and lower side band frequencies of the mixed signal. In one embodiment, the upper side band frequency and the lower side band frequency are higher than the frequency of a detected MRI signal.

At 430, method 400 includes determining a scan plane that will correspond to the orientation of the intervention-independent device. Determining the scan plane includes collecting image data in the MRI system. The image data may include projections in three orthogonal axes for each marker. Determining the scan plane may also include performing Fourier transform operations on the projection in each axis. Determining the scan plane may also include determining a position for a marker with respect to each axis. Magnitude reconstruction may be employed on the output of the Fourier transform operations to determine the positions for the markers with respect to each axis. Determining the scan plane may include constructing a scan plane that intersects the determined positions of the first set of markers.

At 440, method 400 includes automatically controlling an MRI system with which the device is interacting to perform a scan on the determined scan plane. For example, as a surgeon is performing a needle biopsy on a patient, the surgeon may manipulate the glove to cause the MRI system to perform a scan on the scan plane aligned with the orientation of the surgeon's fingers in the glove. Manipulating the glove to control the MRI system in real time (e.g., change scan plane, change other MRI parameters) addresses some of the deficiencies of conventional systems in which a surgeon may need to spend valuable time performing a time consuming manual adjustment of the scan plane.

A surgeon may receive tactile feedback from an interventional device in use on a patient. For example, a surgeon moving a catheter through the vascular system of a patient may receive tactile feedback from the catheter indicating that a bend in an artery has been reached or that a region of hardened arterial plaque has been encountered. Thus, method 400 may include, in response to the tactile feedback, manipulating the hand wearable device to specify a desired scan plane for an MR image. The manipulation of the hand wearable device may be performed without mechanical or signal interaction with the interventional device. Thus, the surgeon may wiggle her fingers in the glove or make other gestures without sending a signal or mechanical force to the interventional device. Receiving tactile feedback from an interventional device in use on a patient while simultaneously manipulating the hand wearable device to specify a desired scan plane for an MR image without having to perform a time consuming manual adjustment of the scan plane improves on conventional systems. Interventional procedures may be completed more quickly because the surgeon does not have to perform the time consuming manual scan plane adjustment.

Additionally, the surgeon may not have to break focus from a real-time MR image to deal with MR apparatus reconfiguration. Furthermore, patient discomfort may be reduced compared to conventional systems. The surgeon may not have to divert their attention from manipulating the interventional device, which reduces the chances that the surgeon will have to re-direct the interventional device through the patient's vasculature.

The plurality of markers may include a second set of two or more markers mounted distally from the proximal interphalangeal joints of the interventionalist. In this embodiment, the members of the second set of markers are mutually exclusive from the first set of markers. For example, the first set of markers may be mounted on the interventionalist's little finger, ring finger, and middle finger, while the second set of markers may be mounted on the interventionalist's index finger and thumb. Thus the first set of markers and the second set of markers are disjoint. Thus, method 400 may also include monitoring the spatial proximities of the second set of markers. Monitoring the spatial proximities means monitoring how close together or how far apart the markers are. Method 400 may also include controlling a switch-based control based, at least in part, on the spatial proximities of the second set of markers. For example, the distance between two of the markers may control the FOV. The switch-based control may control image acquisition parameters including, but not limited to, FOV, phase encoding direction, frequency encoding, pulse sequence, repetition time, echo time, and number of signal averages.

Figure 5:
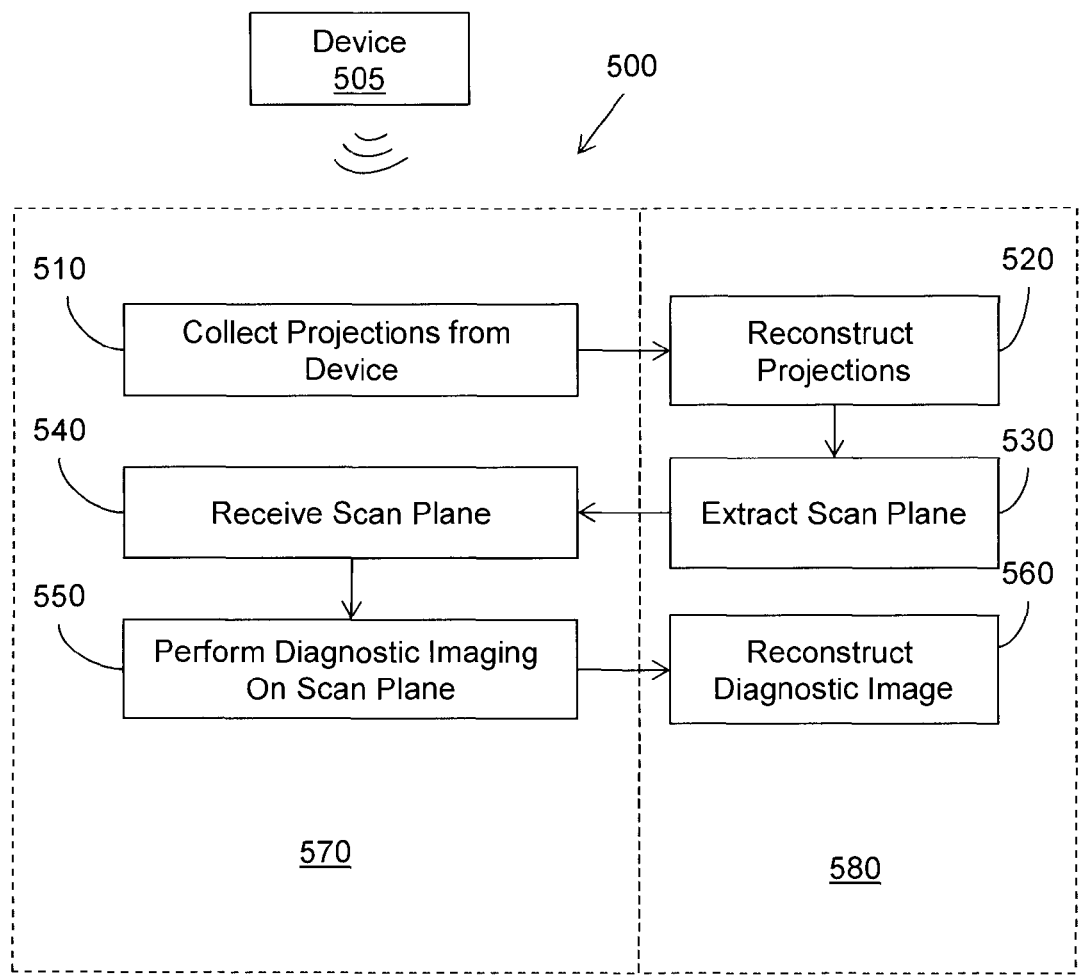
FIG. 5 is a flow diagram that illustrates an example data flow associated with an example method for performing MRI control.

FIG. 5 illustrates a data flow 500. Portions of data flow 500 may occur in image acquisition components 570 of an MRI system 500 or in image reconstruction components 580 of an MRI system 500. The image acquisition components are grouped in area 570 while the image reconstruction components are grouped in area 580. At 510, image data for the markers is collected by the image acquisition components. The image data may include tracking projections in three orthogonal axes. The image data may be acquired from an intervention-independent device 505 (e.g., glove worn on the hand of a surgeon). The image data may be collected using, for example, a FLASH (fast low angle shot MRI) sequence that has been modified to collect the tracking projections. Other pulse sequences may be employed. At 520, the tracking projections are reconstructed by, for example, performing Fourier transform operations on the tracking projections in the axes. At 520, a position with respect to the axes for the markers may be determined. The position may be determined using magnitude reconstruction on the output of the Fourier transform operations. At 530, a scan plane that intersects the determined position of the markers is extracted.

At 540, the scan plane to be used to acquire images is received in the image acquisition components 570. The image acquisition components 570 may then perform diagnostic imaging at 550 using the scan plane. At 560, image data is reconstructed into a diagnostic image for display. The reconstructed image produced by data flow 500 is independent of device 505 and is determined by the position data received from the device 505.

Figure 6:
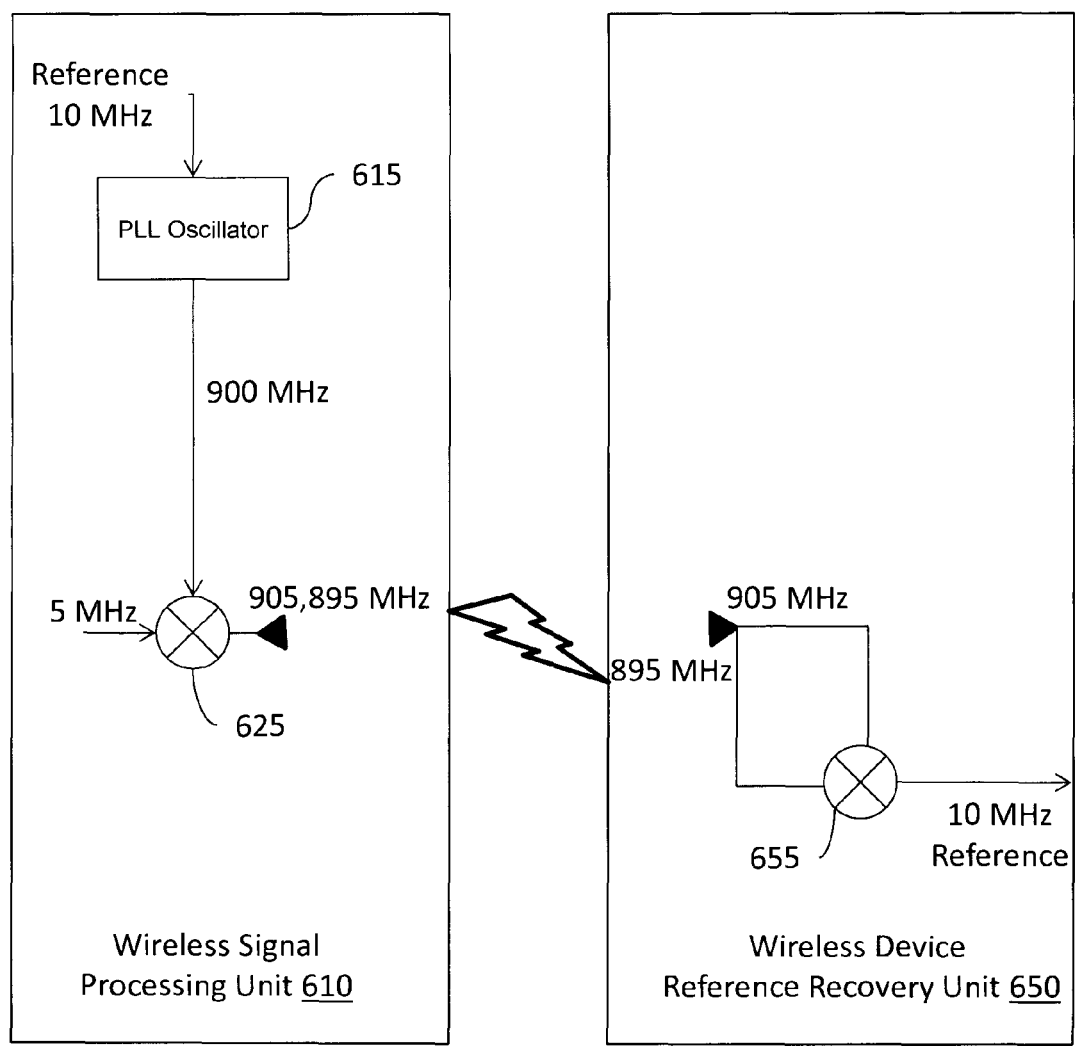
FIG. 6 schematically illustrates an embodiment of a reference signal recovery system associated with intervention-independent scan plane control.

FIG. 6 illustrates wirelessly transmitting a reference signal from a wireless signal processing unit 610 to a wireless device reference recovery unit 650. The reference signal is used to synchronize an intervention-independent device (e.g., glove worn on hand of surgeon) to an MRI system with which the device is interacting. The MRI system receives and responds to position data from the intervention-independent device. FIG. 6 illustrates a low frequency 10 MHz reference signal. Other reference signals may be employed. The low frequency signal may be provided by the MR scanner to synchronize electronics in the MR scanner. Generally, the hand-wearable device may be controlled, at least in part, by the synchronizing signal from the MR scanner. However, in the embodiments illustrated in FIGS. 7 and 8, a different approach is illustrated.

A phase locked loop (PLL) oscillator circuit 615 generates a high frequency (e.g., 900 MHz) carrier frequency signal. The high frequency carrier frequency signal is mixed with a 5 MHz signal by mixer 625 to produce sideband component frequencies of 905 MHz and 895 MHz. The sideband component frequencies are transmitted to a wireless device reference recovery unit 650 on the intervention-independent device. The reference recovery unit 650 receives the high frequency upper and lower sideband components and mixes them with mixer 655 to recover the low frequency reference signal of 10 MHz.

Figure 7:
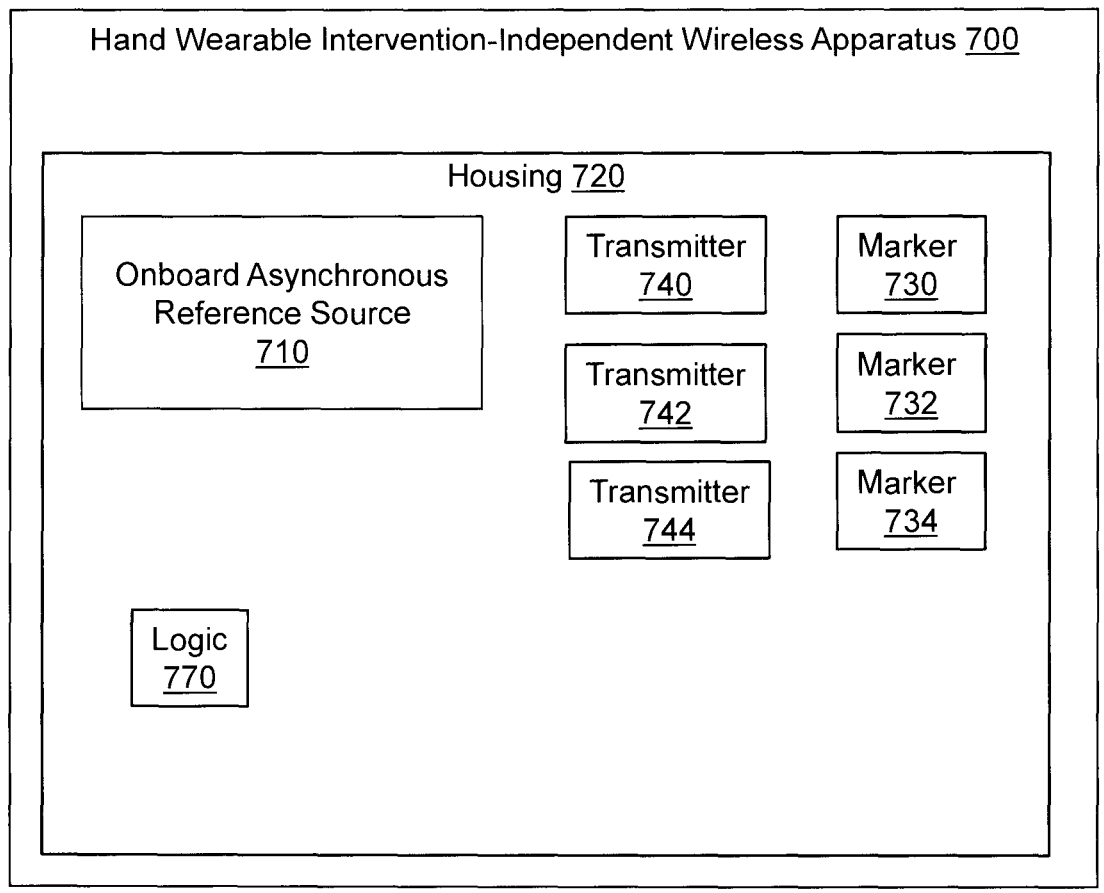
FIG. 7 illustrates an example hand wearable wireless apparatus for use in an MRI system.

FIG. 7 illustrates a hand wearable intervention-independent wireless apparatus 700 for MRI scan plane control. Apparatus 700 may be, for example, a glove. Apparatus 700 may be used in conjunction with an MRI system. Apparatus 700 includes markers 730, 732, and 734 that produce position signals corresponding to the positions of the markers 730, 732, and 734. The position signals describe an orientation of the apparatus 700. The position signals are magnetic resonance signals from which the spatial coordinates of a marker or the orientation of a marker are determined. The position signals can be used to describe a desired MR scan plane. The desired scan plane controls the MRI system to perform a subsequent scan of the patient along the scan plane. Unlike conventional systems, the scan plane may be determined without considering a position of an interventional device in the patient. A surgeon moving a laser ablation device inside the heart of a patient with her right hand may be controlling the MRI apparatus by moving her fingers in the glove on her left hand. In one embodiment, the position signals control a switch-based control that controls image acquisition parameters. Markers 730, 732, and 734 may be active markers that are responsive to excitation from an MRI magnetic field to produce the position signals. In one embodiment, the markers 730, 732, and 734 may be orthogonal solenoid coils connected in series. The orthogonal solenoid coils may be wrapped around a fiducial marker.

Apparatus 700 includes transmitters 740, 742, and 744. Transmitters 740, 742, and 744 transmit the position signals produced by markers 730, 732, and 734 to an MRI system. While three transmitters 740, 742, and 744 are illustrated, a greater or lesser number of transmitters may be employed.

Apparatus 700 includes a housing 720 that houses the markers 730, 732, and 734 and the transmitters 740, 742, and 744. Housing 720 may be worn by a surgeon. For example, housing 720 may be worn on the hand or wrist. In one embodiment, housing 720 is a glove. In another embodiment, housing 720 is a mitten. Housing 720 may mount the markers distally to a proximal interphalangeal joint of a finger. Housing 720 may also mount a marker distally to a proximal interphalangeal joint of the thumb. In one embodiment, markers may be mounted dorsally to the hand or wrist. In other embodiments, markers may be mounted in other positions relative to the hand or wrist. In one embodiment, housing 720 allows a marker mounted distally to the proximal interphalangeal joint of the finger and a marker mounted distally to the proximal interphalangeal joint of the thumb to move within a threshold of the range of motion of the fingers and thumb if the apparatus 700 was not being worn. In this embodiment, housing 720 mounts transmitters 740, 742, and 744 within a threshold distance of the wrist.

Apparatus 700 may be used in the bore of an MRI system. Apparatus 700 may be used to control the MRI system. The MRI system may control one or more of its elements using a synchronization signal. In this embodiment, hand wearable wireless intervention-independent apparatus 700 generates its own onboard asynchronous reference signal using onboard asynchronous reference source 710. Onboard asynchronous reference source 710 produces a reference signal asynchronous to a synchronous signal. In one example, the asynchronous reference signal is asynchronous to the synchronization signal provided by an MR scanner as described above. Apparatus 700 includes a logic 770 that may be controlled by the reference signal. The onboard asynchronous reference source 710 produces a carrier frequency to transmit signals from the apparatus 700 to the MRI system.

In one example, the onboard asynchronous reference source 710 is a ceramic oscillator. Recall that apparatus 700 may be employed in an MRI bore and thus may be subjected to intense magnetic fields (e.g., 1.5 T, 3 T, 7 T). In one example, the ceramic oscillator may be a 5 MHz ceramic oscillator. In another example, the ceramic oscillator may be a 10 MHz ceramic oscillator. Other frequencies (e.g., 20 MHz) may be employed. For example, the onboard asynchronous reference source 710 may be a ceramic oscillator in the range of 1 MHz to 100 MHz. In one example, the ceramic oscillator will produce a signal whose frequency shift error is less than 20 ppm. Signals with other qualities (e.g., frequency shift error up to 100 ppm) may be generated. For example, the 10 MHz ceramic oscillator may produce the reference signal with a frequency shift error of less than 100 ppm.

Figure 8:
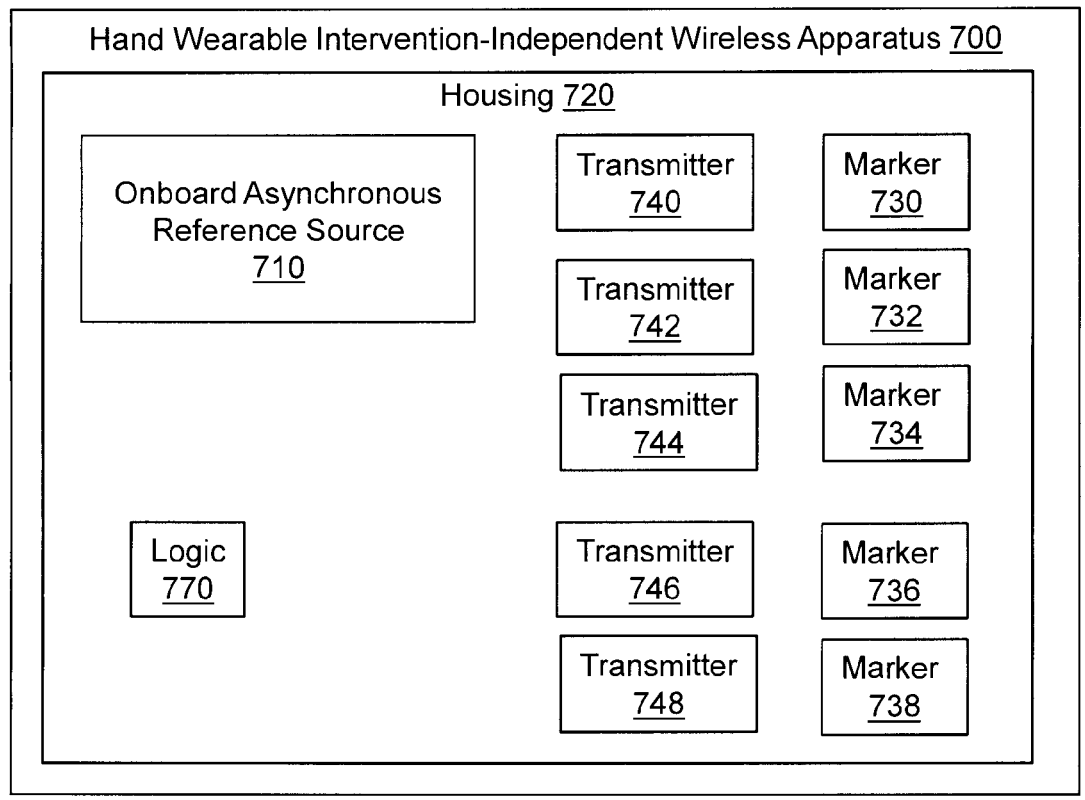
FIG. 8 illustrates an example hand wearable wireless apparatus for use in an MRI system.

FIG. 8 illustrates another embodiment of hand wearable wireless apparatus 700. This embodiment of apparatus 700 includes the three markers 730, 732, 734 that produce position signals sufficient to describe a desired MR scan plane. This embodiment of apparatus 700 also includes two additional markers 736 and 738 that produce position signals sufficient to control a switch based control. The switch based control may control image acquisition parameters (e.g., FOV, pulse sequence, TE, TR) for an MRI apparatus. In this embodiment of apparatus 700, the markers 730, 732, and 734 are mounted dorsally to the fingertips of the little finger, ring finger, and middle finger respectively. The scan plane is constructed from the position signals generated by markers 730, 732, and 734. For example, the scan plane may intersect the determined positions of the markers 730, 732, and 734. In this embodiment of apparatus 700, the markers 736 and 738 are mounted dorsally to the fingertips of the index finger and thumb respectively. In this example, moving marker 736 closer to the marker 738 can generate a control signal. The control signal may be used to switch through predefined FOV shifts for the acquired image or to perform other actions. Other image acquisition parameters, including phase encoding direction and repetition time may be controlled by the switch based control. Thus, in this embodiment of apparatus 700, three markers are placed on three fingers and are used for controlling the scan plane while two markers are placed on the other finger and thumb and are available to control the switch based control.

When a surgeon or radiologist performs an interventional procedure on a patient, one of the challenges faced by the surgeon is how to guide the interventional device to the target region of the patient's body. For example, a radiologist may wish to guide a catheter through a patient's vascular system to a region in the patient's neck. Magnetic resonance imaging (MRI) may be used to provide a view into the patient's body to let the radiologist see the catheter. A wireless device worn on the radiologist's non-catheter hand lets the radiologist control the catheter with one hand while simultaneously controlling the MRI system with the other hand. Since the radiologist's hands are inside the MRI magnet bore with the patient, the device worn on one of the radiologist's hands uses the magnetic field in the MRI bore to generate signals from markers located on the device. These position signals are generated independently of signals generated by the catheter. In this example, the device is a glove, and the markers are attached to the fingertips of the glove. These independently generated signals are wirelessly transmitted to the MRI system and let the radiologist control both the orientation, (e.g., scan plane) of the images produced by the MRI system and the parameters the MRI system uses to acquire the image (e.g. field of view) simply by moving her hand and fingers. Because the device is wireless and operates in real time, the radiologist has improved freedom to find the most useful scan plane using the most appropriate imaging parameters. This increases the chance the procedure will be successful, and reduces the amount of time the patient has to spend in the MRI magnet bore.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Logic", as used herein, includes but is not limited to hardware, firmware, software in execution on a machine, or combinations of each to perform a function(s) or an action(s), or to cause a function or action from another logic, method, or system. Logic may include a software controlled microprocessor, a discrete logic (e.g., ASIC), an analog circuit, a digital circuit, a programmed logic device, a memory device containing instructions, and other physical devices. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. An intervention-independent device for magnetic resonance imaging control, comprising:
    a plurality of markers that produce position signals corresponding to positions of members of the plurality of markers, where the position signals describe an orientation of the device, where the position signals are magnetic resonance (MR) signals from which the spatial coordinates of a member of the plurality of markers or the orientation of the device can be determined, where the position signals are sufficient to describe a desired MR scan plane, and where members of the plurality of markers comprise active markers that are responsive to excitation from the MRI magnetic field to produce the position signals;
    one or more transmitters that transmit the position signals to an MRI system using amplitude modulation or frequency modulation;
    a wireless reference recovery unit that receives the position signals;
    an onboard asynchronous reference source that produces a reference signal asynchronous to a synchronization signal associated with the MRI system and produces a carrier frequency to transmit the position signals;
    a housing that houses the plurality of markers, the one or more transmitters, and the onboard asynchronous reference source, where the housing is wearable on a hand or a wrist of an interventionist performing an MRI-aided intervention on a patient, where the housing mounts a first member of the plurality of markers distally to a proximal interphalangeal joint of a finger of the interventionist, where the housing mounts a second member of the plurality of markers distally to a proximal interphalangeal joint of the thumb of the interventionist, where the housing mounts the one or more transmitters within a threshold distance of the wrist of the interventionist, and where members of the plurality of markers are connected to members of the one or more transmitters;
    where the plurality of markers and the one or more transmitters operate without signal or mechanical interaction with an interventional device in use during the MRI-aided intervention on the patient; and
    where the desired scan plane controls the MRI system to perform a scan of the patient along the scan plane independent of a position of the interventional device.

2. The device of claim 1, the onboard asynchronous reference source being a ceramic oscillator having an oscillation frequency in the range of 5 MHz to 10 MHz that produces the reference signal with a frequency shift error in the range of 1 ppm to 100 ppm.

3. The device of claim 1, where the housing is a glove, where the plurality of markers mounted on the housing move within a threshold of the degree of freedom of movement of the hand of the interventionalist.

4. The device of claim 1, comprising a switch-based control, where spatial proximities of members of the plurality of markers are derived from the position signals, and where the spatial proximities control the switch-based control.

5. The device of claim 4, where the switch-based control controls image acquisition parameters including one or more of, field of view (FOV), phase encoding direction, frequency encoding, pulse sequence, repetition time, echo time, and number of signal averages.

6. The device of claim 5, where the desired MR scan plane position is described by position signals produced by members of the plurality of markers mounted within a threshold distance of two of the fingers of the interventionalist and by a member of the plurality of markers mounted within a threshold distance the thumb of the interventionalist, and where the switch-based control is controlled by the relationship of position signals produced by a member of the plurality of markers mounted within a threshold distance of at least one of the fingers of the interventionalist not used to produce positions signals that describe the desired MR scan plane, and the position signal produced by the member of the plurality of markers mounted within a threshold distance of the thumb of the interventionalist.

7. The device of claim 5, where the desired MR scan plane position is described by position signals produced by members of the plurality of markers mounted within a threshold distance of the little finger of the interventionalist, the ring finger of the interventionalist, and middle finger of the interventionalist, and where the switch-based control is controlled by the relationship of a position signal produced by a member of the plurality of markers mounted within a threshold distance of the index finger of the interventionalist and the position signal produced by the member of the plurality of markers mounted within a threshold distance of the thumb of the interventionalist.

8. The device of claim 1, the interventional device being one of, a needle, a catheter, an ablative device, a diagnostic device, and a therapeutic device.

9. The device of claim 1, where a member of the plurality of markers comprises a fiducial marker coupled to a microcoil.

10. The device of claim 1, where a member of the plurality of markers comprises a plurality of orthogonal solenoid coils connected in series, where the orthogonal solenoid coils are wrapped around a fiducial marker.

11. The device of claim 1, where the wireless reference recovery unit receives a mixed signal comprising high frequency upper and lower sideband components of a low frequency reference signal and mixes the received high frequency upper and lower sideband components to recover the low frequency reference signal, where the reference signal is used to synchronize the device with the MRI system for wireless communication, the high frequency upper sideband being a greater frequency than the high frequency lower sideband, the high frequency upper sideband and high frequency lower sideband having a greater frequency than the lower frequency reference signal.

12. A method for automatically controlling an MRI system being used in an MRI-guided procedure involving an interventional device inserted in a patient, comprising:
- wirelessly receiving, in the MRI system, from a wearable device being manipulated by an interventionalist independently of the interventional device, position signals describing an orientation of the wearable device,
- where the receiving is performed by wirelessly receiving amplitude modulated signals describing an orientation of the hand wearable device or frequency modulated signals describing an orientation of the wearable device,
- where the wearable device comprises a plurality of markers, where the plurality of markers comprises a first set of three or more markers mounted distally from the proximal interphalangeal joints of the interventionalist;
- wirelessly receiving a reference signal for use in synchronizing the position signals from the wearable device with the MRI system, where receiving the reference signal comprises:
  - receiving a mixed signal comprising high frequency upper and lower side band frequencies for a low frequency reference signal; and
  - reconstructing the low frequency reference signal by mixing the upper and lower side band frequencies of the mixed signal,
  - where the upper side band frequency and the lower side band frequency are higher than the frequency of a detected MRI signal;
- determining a scan plane that will correspond to the orientation of the device by:
  - collecting, in the MRI system, image data including projections in three orthogonal axes for members of the first set of markers;
  - performing Fourier transform operations on the projections in the three orthogonal axes;
  - determining a position with respect to the three orthogonal axis for members of the first set of markers using magnitude reconstruction on the output of the Fourier transform operations; and
  - constructing a scan plane that intersects the determined positions of the first set of markers; and
- automatically controlling the MRI system to perform a scan on the determined scan plane.

13. The method of claim 12 comprising:
- receiving tactile feedback from the interventional device; and
- in response to the tactile feedback, manipulating the wearable device to specify a desired scan plane for an MR image to be acquired by the MRI system, where the manipulation of the wearable device is performed without mechanical or signal interaction with the interventional device.

14. The method of claim 12, where the plurality of markers comprises a second set of two or more markers mounted distally from the proximal interphalangeal joints of the interventionalist, where the second set of markers is mutually exclusive with the first set of markers.

15. The method of claim 14, comprising:
- monitoring spatial proximities of the positions of members of the second set of markers; and
- controlling a switch-based control based, at least in part, on the spatial proximities of the positions of the members of the second set of markers.

16. An intervention-independent apparatus for magnetic resonance imaging (MRI) scan plane control, comprising:
- a plurality of markers that produce position signals corresponding to positions of members of the plurality of markers,
  - where the position signals describe an orientation of the apparatus,
  - where the position signals are magnetic resonance signals from which the spatial coordinates of a member of the plurality of markers or the orientation of a member of the plurality of markers can be determined,
  - where the position signals describe a desired magnetic resonance (MR) scan plane,
  - where the position signals control a switch-based control that controls image acquisition parameters, and
  - where members of the plurality of markers comprise active markers that are responsive to excitation from the MRI magnetic field to produce the position signals;
- one or more transmitters that transmit the position signals to an MRI system; and
- a housing that houses the plurality of markers and the one or more transmitters,
  - where the housing is wearable on a hand or a wrist of an interventionalist,
  - where the housing mounts a first member of the plurality of markers distally to a proximal interphalangeal joint of the finger of the interventionalist,
  - where the housing mounts a second member of the plurality of markers distally to a proximal interphalangeal joint of the thumb of the interventionalist,
  - where the housing allows the first member of the plurality of markers and the second member of the plurality of markers to move within a threshold of the range of motion of the fingers and thumb of the interventionalist,
  - where the housing mounts the one or more transmitters within a threshold distance of the wrist of the interventionist, and
  - where a member of the plurality of markers is connected to a member of the one or more transmitters;
- where the desired scan plane controls the MRI system to perform a subsequent scan of the patient along the scan plane independent of a position of the interventional device.

17. The apparatus of claim 16, where the apparatus is used in the bore of an MRI system that controls one or more elements of the MRI system using a synchronization signal, the apparatus comprising:
- an onboard asynchronous reference source that produces a reference signal asynchronous to a synchronization signal, and
- a logic controlled by the reference signal,
- where the onboard asynchronous reference source produces a carrier frequency to transmit one or more signals from the apparatus to the MRI system.

18. The apparatus of claim 17, the onboard asynchronous reference source being a 5 MHz ceramic oscillator that produces the reference signal with a frequency shift error of less than 20 ppm.

19. The apparatus of claim 17, the onboard asynchronous reference source being a 10 MHz ceramic oscillator that produces the reference signal with a frequency shift error of less than 100 ppm.

20. The apparatus of claim 17, the onboard asynchronous reference source being a ceramic oscillator in the range of a 1 MHz oscillator to a 100 MHz oscillator.

21. The apparatus of claim 20, the onboard asynchronous reference source being configured to produce the reference signal with a frequency shift error of less than 200 ppm.

22. An apparatus for magnetic resonance imaging (MRI) scan plane control, comprising:

- a plurality of markers that produce position signals corresponding to positions of members of the plurality of markers,
  - where the position signals are magnetic resonance signals from which the spatial coordinates of a member of the plurality of markers can be determined,
  - where the position signals describe an orientation of the apparatus,
  - where the position signals describe a desired magnetic resonance (MR) scan plane,
  - where the position signals control a switch-based control that controls image acquisition parameters, and
  - where members of the plurality of markers comprise active markers that are responsive to excitation from an MRI magnetic field to produce the position signals;
- one or more transmitters that transmit the position signals to an MRI system; and
- a housing that houses the plurality of markers and the one or more transmitters, where the housing is wearable on a hand or a wrist of a person whose hand is in the MRI magnetic field, where the housing mounts the one or more transmitters within a threshold distance of the wrist of the interventionist, and where a member of the plurality of markers is connected to a member of the one or more transmitters;
- where the desired scan plane controls the MRI system to perform a subsequent scan of the patient along the scan plane.

* * * * *